United States Patent [19]

Jones

[11] 4,203,316

[45] May 20, 1980

[54] DEVICE AND METHOD FOR CALIBRATING PULMONARY FUNCTION TESTING EQUIPMENT

[75] Inventor: William C. Jones, Oak Brook, Ill.

[73] Assignee: Jones Medical Instrument Company, Oak Brook, Ill.

[21] Appl. No.: 37,409

[22] Filed: May 9, 1979

Related U.S. Application Data

[63] Continuation-in-part of Ser. No. 947,195, Sep. 29, 1978, abandoned.

[51] Int. Cl.² ............................................. G01F 25/00
[52] U.S. Cl. .......................................................... 73/3
[58] Field of Search ...................... 73/3, 279; 128/725, 128/726, 727, 728, 729

[56] References Cited

U.S. PATENT DOCUMENTS

| | | | |
|---|---|---|---|
| 3,086,515 | 4/1963 | Jones | 128/728 |
| 3,512,521 | 5/1970 | Jones | 128/728 |
| 3,589,190 | 6/1971 | Jones | 73/279 |

*Primary Examiner*—Donald O. Woodiel
*Attorney, Agent, or Firm*—Tilton, Fallon, Lungmus & Chestnut

[57] ABSTRACT

A device and method for calibrating pulmonary function testing equipment by discharging a precise volume of compressed gas at reproducible and substantially exponentially diminishing flow rates through an orifice of a selected size into such equipment. The device includes a container defining a chamber for containing a predetermined volume of gas at a preselected pressure, a gas discharge conduit, which may serve as a conversion or expansion chamber, communicating with the container and having a flow-restricting fixed orifice of predetermined size for the discharge of gas, and a mechanism normally preventing the discharge of gas from the device but being selectively operable to release the gas through the orifice at reproducible and substantially exponentially diminishing flow rates into a spirometer for calibrating that instrument. In one form of the invention, there is provided an isolation housing having a pair of chambers, one of which communicates with the gas-discharging device and the other with the remainder of the pulmonary function testing equipment, the chambers of the housing being separated by a flexible barrier which prevents intermixing of the gaseous contents of the respective chambers. One or more heating elements may also be provided so that the air discharged into the pulmonary function testing equipment will be warmed to body temperature.

37 Claims, 14 Drawing Figures

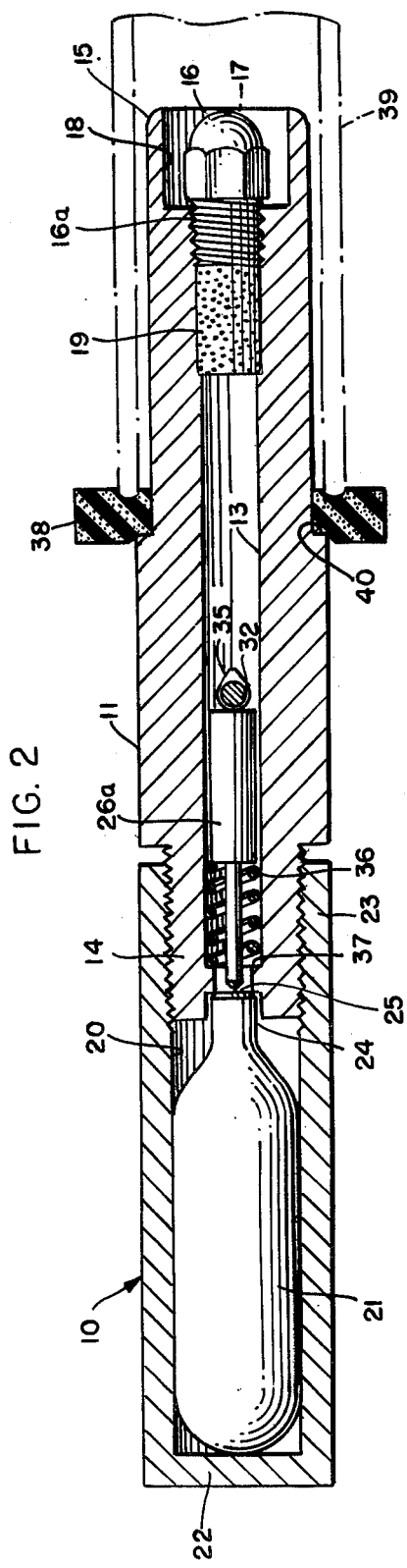
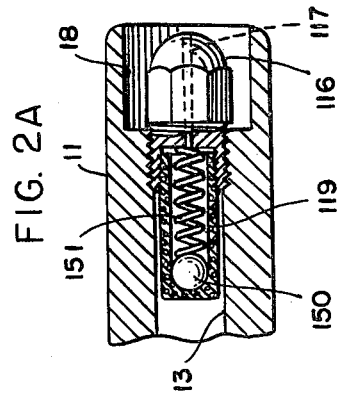
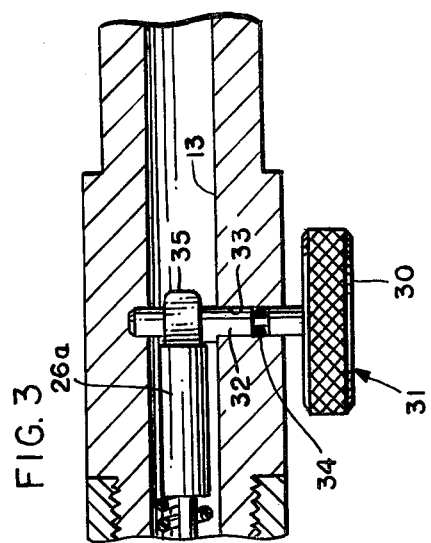
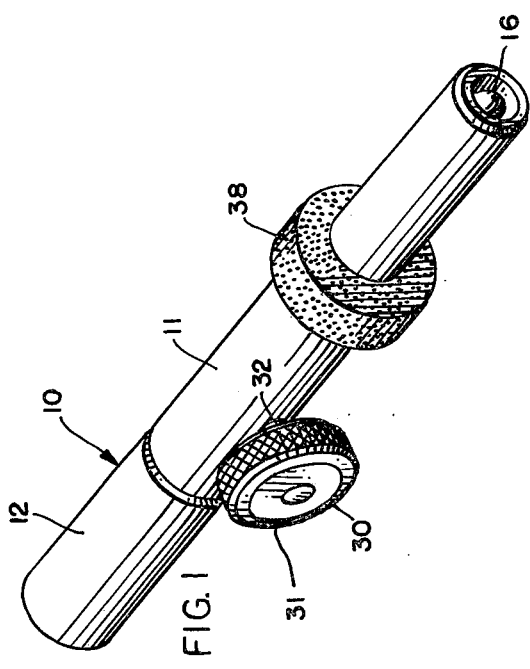

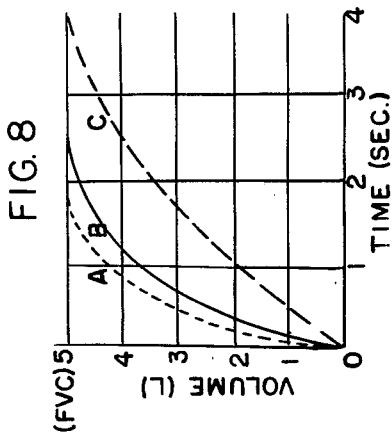
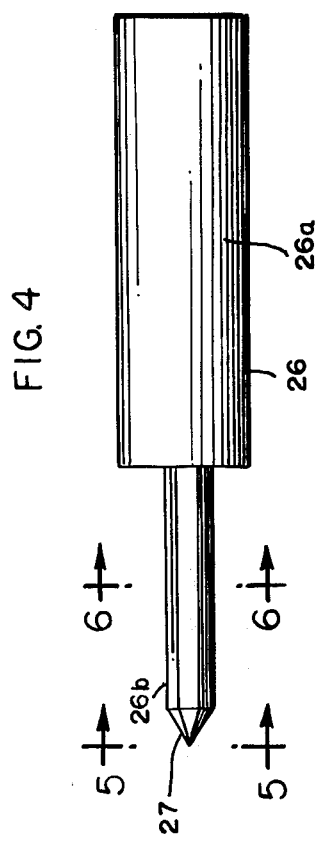
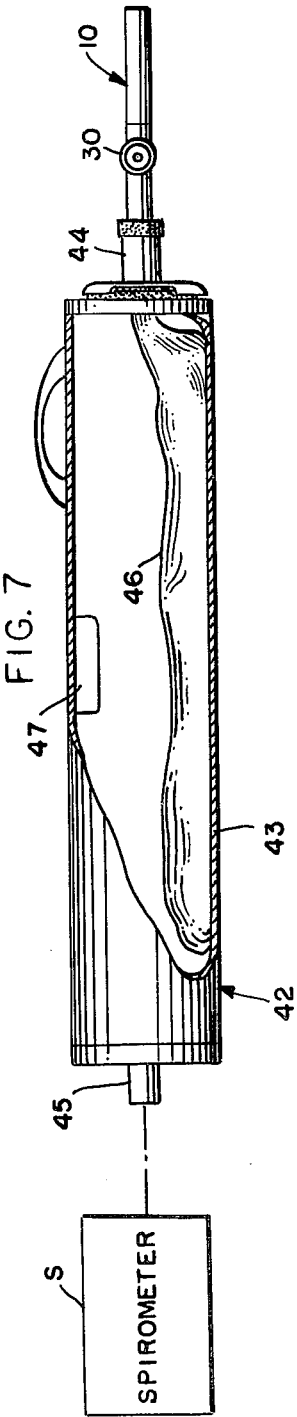

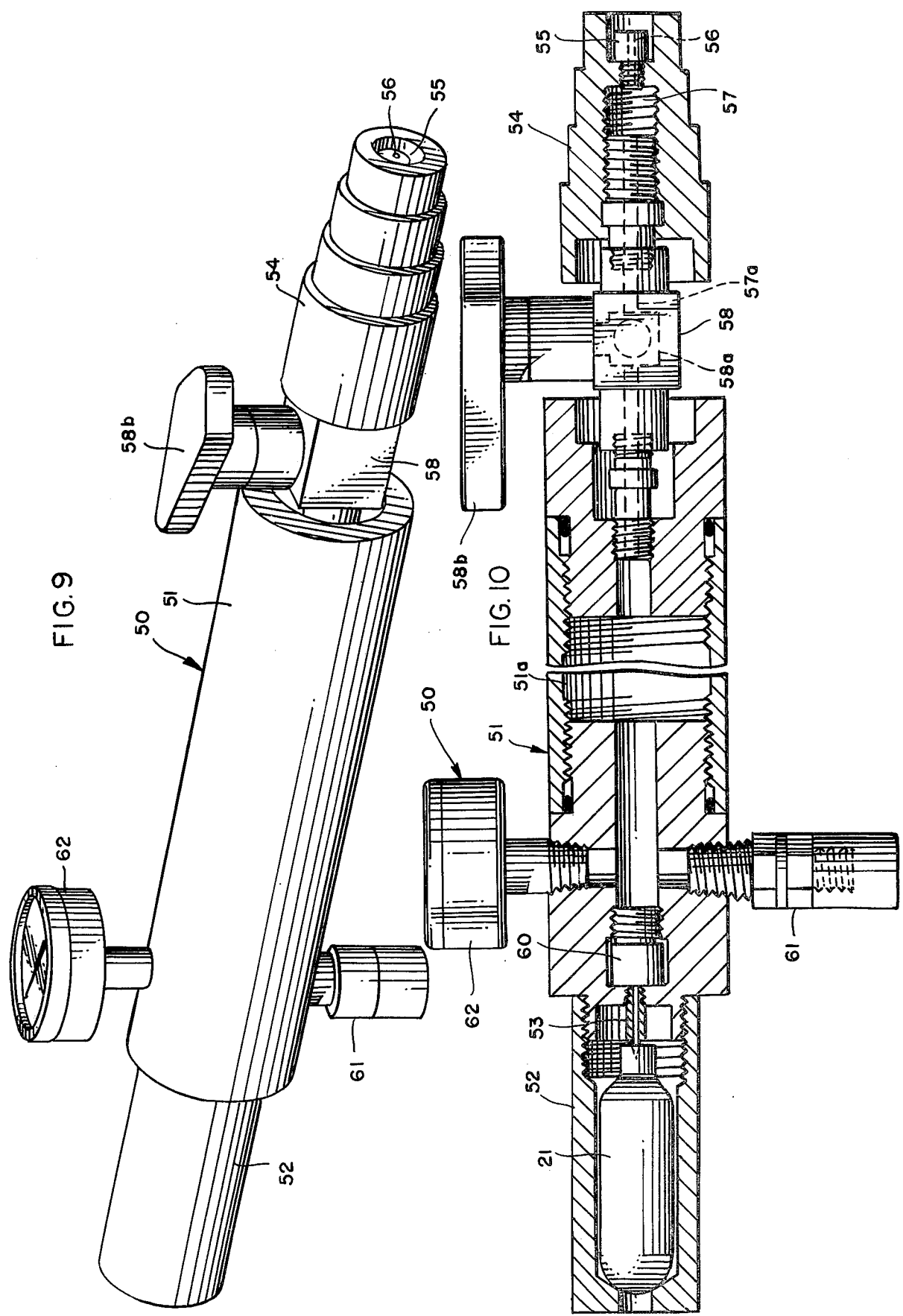

DEVICE AND METHOD FOR CALIBRATING PULMONARY FUNCTION TESTING EQUIPMENT

RELATED APPLICATION

This application is a continuation-in-part of my co-pending application, Ser. No. 947,195, filed Sept. 29, 1978, now abandoned.

BACKGROUND

In recent years there has been an increasing awareness of the prevalence of lung function abnormalities, resulting in mass testing programs, industrial health surveillance programs, and federal disability evaluations, as well as initial detection of differential diagnosis in a variety of medical environments.

U.S. Pat. Nos. 3,086,515 and 3,589,190 disclose bellows-type pulmonary function testing equipment; other types include manometer systems in which an inverted cannister is supported for vertical movement while being partially emmersed in a body of liquid, and electronic systems in which volume and flow rates are electronically measured. All such systems, which are commonly utilized for measuring Forced Vital Capacity (FVC) and changing flow rates represented by Forced Expiratory Volumes (FEV), are commonly referred to as "spirometers".

Although the spirometers disclosed in the afore-mentioned patents, as well as other known spirometer constructions, have been proven for their reliability and accuracy, there have been various uncertainties relating, for example, to possible leakage of the volume collecting devices, or to possible variations in chart timer speed from one instrument to the next. Also, some of the newer electronic spirometers have been proclaimed as advantageous but there has been little available to test their validity or correlate their values to the classic prediction normal standards.

The basic pulmonary function test requires a subject to maximally expire air and then forcefully exhale all of his distendible lung volume as quickly (to assess flow obstruction) and completely (to assess volumetric restrictions) as possible. As it is the repeatability of results that serves as the guide to prove validity, it is also important that the testing device is itself repeatable in simultaneously deriving flow and volume values.

Applicant has previously developed and disclosed the use of a large cylinder with a piston having a geared rack driven by a one-third horsepower geared synchronous motor for the purpose of testing the performance of spirometers. Such an apparatus is designed to discharge a precise volume of gas at uniform flow rates and is both bulky and expensive, characteristics which render such calibrating equipment unsuitable for use in the periodic (preferably daily) checking of spirometers in field use. Although the need for an inexpensive, compact, and easily operated device for calibrating spirometers has been recognized for a number of years, devices meeting those requirements have not heretofore been known or become available.

SUMMARY

An important aspect of this invention lies in providing a simple, inexpensive means for calibrating spirometers on a day-to-day basis, providing precisely repeatable time-volume and/or flow-volume curves, and providing records for assessing volume-time-flow artifacts and timing speed. A further object is to provide a method and a device for quickly checking the performance of a spirometer under precisely reproducible conditions which simulate those encountered in actual pulmonary function tests; that is, the testing gas is discharged into the spirometer in a selected period of short duration and at essentially exponentially diminishing flow rates.

Another object of this invention is to provide a system which produces a record that may be easily corrected to BTPS (body temperature, barometric pressure, moisture saturated) conditions under which comparative prediction standards are based. In that connection, it is a specific object to provide a system utilizing a heat generator for obviating the necessity of BTPS and other corrections involved with a calibration procedure.

In one embodiment, the device takes the form of a compact holder having a cartridge-receiving section and a body section. The cartridge-receiving section is adapted to receive pressurized gas cartridges which bear superficial resemblance to the cartridges used in beverage dispensers. The body section is provided with a piercing element for piercing the seal of the cartridge held within the cavity of the other section, the piercing element being operable to pierce the seal of the cartridge upon manipulation by the user of an operating handle or knob. When the handle is so operated, a precise volume of pressurized gas is discharged through a fixed orifice of the body section at essentially exponentially diminishing flow rates and over an interval similar to the time intervals encountered in conducting a pulmonary function test. The gas is discharged from the orifice into the mouthpiece of the spirometer to which the body section is hermetically coupled.

The mouthpiece may take the form of the inlet tube of an isolation housing similar to the breath isolator disclosed in U.S. Pat. No. 3,512,521. Such an isolator comprises a housing of fixed total volume having a pair of chambers separated by an impermeable membrane in the form of a bag disposed within the housing and communicating directly with the inlet. Expansion of the bag by gas discharged from a pierced cartridge causes an equal volume of air to be displaced from the outlet of the isolator housing. That outlet communicates directly with the spirometer which in turn measures the volume and flow rates of the displaced air. Consequently, the gas actually measured (air) by the spirometer is closely in composition to exhaled air than the gas discharged directly from the pierced cartridge (usually carbon dioxide), the flow characteristics of the air are more uniform over the cross sectional area of the spirometer's inlet tube than they would be for pressurized gas discharged directly into that tube from a pierced cartridge, and the temperature of the gas (air) entering the spirometer may be more readily established and controlled. A heating element may be disposed within the isolation housing to heat the air therein to body temperature, thereby eliminating the need for subsequent BTPS correction or for gas temperature drop due to rapid expansion of the pressurized gas, the latter being substantial when capsulized carbon dioxide is expanded from its liquid state.

In another embodiment of the invention, the pressurized contents of a disposable cartridge are first discharged into a conversion chamber equipped with a pressure relief valve which is preset to control the maximum pressure, and hence the volume, of the gas within that chamber. The gas-releasing mechanism takes the form of a valve which may then be shifted into an open position to discharge the pressurized gas from the conversion chamber into the expandable chamber of a spirometer, or into a breath isolator connected to the mouthpiece of a spirometer.

In a further form of the invention, the container is reusable and is pressurized in advance of each instrument-calibrating procedure by means of a suitable pump. The disclosed embodiment also includes a pressure gauge, a relief valve, and a solenoid valve for properly controlling the operation of the system. If desired, all of the major components of that system may be housed within a spirometer casing so that the calibrating apparatus is always readily available to confirm the reliability and accuracy of the spirometer.

In all forms of the invention, a precisely-controlled volume of pressurized gas is discharged from a rigid container through a fixed orifice into the expandable chamber of a spirometer at essentially exponentially diminishing flow rates.

Other features, advantages, and objects of the invention will become apparent from the drawings and detailed description.

Drawings

FIG. 1 is a perspective view of a spirometer calibrating device embodying this invention.

FIG. 2 is a vertical longitudinal sectional view of the device, such device being shown in conjunction with the mouthpiece of a spirometer (phantom lines).

FIG. 2A is a fragmentary longitudinal sectional view of the device with a modified filter assembly.

FIG. 3 is a fragmentary horizontal longitudinal sectional view of the device.

FIG. 4 is an enlarged side elevational view of the cartridge piercing element of the device.

FIG. 5 is a further enlarged end view taken along line 5—5 of FIG. 4.

FIG. 6 is an enlarged cross sectional view taken along line 6—6 of FIG. 4.

FIG. 7 illustrates the calibrating device in combination with a gas isolator and spirometer.

FIG. 8 depicts a typical volume/time curve obtained from a spirometer coupled to the calibrating device of this invention.

FIG. 9 is a perspective view of a spirometer calibrating device constituting a second embodiment of this invention.

FIG. 10 is a longitudinal vertical sectional view of the second embodiment.

Detailed Description

Figure 11:
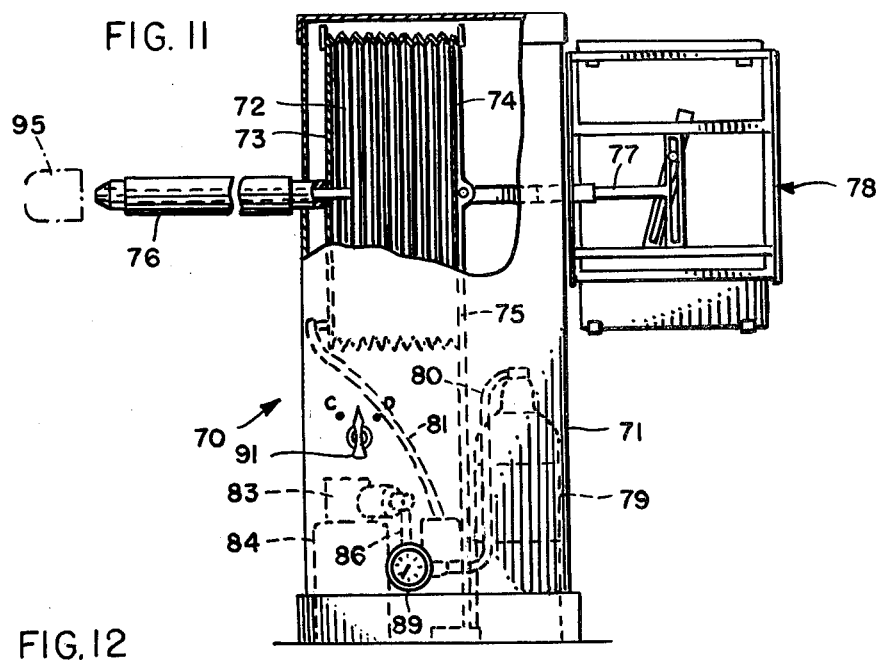
FIG. 11 is a side elevational view of a spirometer equipped with instrument-calibrating means constituting a third embodiment of this invention.

Referring to FIGS. 1–3 of the drawings, the numeral 10 generally designates a calibrating device in the form of a holder having a body section 11 and a cartridge-receiving section 12. The cylindrical body section has an axially-extending expansion chamber or passage 13 extending from the externally-threaded rear end portion 14 to the recessed front or nose portion 15. As shown most clearly in FIG. 2, a nozzle 16 having a fixed orifice 17 is mounted within the recess 18 of the nose portion. The nozzle includes a threaded neck 16a received within the front end of the expansion chamber or passage 13. A filter element 19 formed of sintered metal or other rigid porous material capable of withstanding the forceful discharge of gas at low temperatures is disposed at the front end of the expansion chamber immediately before nozzle 16.

Section 12 is also generally cylindrical in shape and defines a chamber or cavity 20 for receiving a pressurized gas cartridge 21. End wall 22 closes off the rear end of cavity 20 and bears against the rear end of the cartridge to hold that cartridge in the operative position shown. The internally threaded neck portion 23 of section 12 sealingly engages portion 14 of the body so that any gas escaping from cartridge 21 must pass into expansion chamber or passage 13 when the parts are assembled as shown.

The cartridge 21 as shown is similar to a standard carbon dioxide cartridge except perhaps for the precise quantity or weight of its charge. It is to be understood, however, that the cartridge can also take the form of any rigid chamber capable of being repetitively recharged by any means, such as a compressor or hospital gas pressure line, delivering a variety of pressure-volume gas wave forms. The contents of the cartridge have been described as being pressurized gas; however, it is to be understood that such pressurization would ordinarily be carried to the point where the contents of the cartridge are in liquid form. Where liquid carbon dioxide is used, effective results have been obtained where the contents by weight fall within the range of 9 to 14 grams. Whatever particular weight is selected within that range, the variance should not exceed 1.0%. Particularly effective results have been obtained within cartridges loaded with 11.5 grams liquid carbon dioxide, with a maximum variation above or below that weight being no greater than 0.05 grams. Although carbon dioxide is believed to be a highly effective fill for such cartridges, it is apparent that other pressurized gases, either in gaseous or liquid form, may be used.

Cartridge 21 has a tapered neck 24 terminating in a piercable membrane or plug 25 disposed in axial alignment with expansion chamber or passage 13. Gas-releasing means in the form of a reciprocable piercing member 26 is disposed within chamber 13, such member having an enlarged piston portion 26a and a reduced spike portion 26b. The piston portion 26a may be of cylindrical configuration as indicated or, if desired, may be of non-circular cross sectional configuration. In either case, there must be sufficient clearance between the outer surface of expansion chamber 13 to permit gas (or vaporizing liquid) to flow forwardly about the piston when the seal of cartridge 21 is broken.

Spike portion 26b has a pointed tip defined by the convergence of a plurality of planar faces 28 (FIG. 5). While four such faces are shown, a greater or smaller number may be provided as desired. Longitudinal channels 29 are formed along spike 26b to permit the escape of carbon dioxide as soon as the tip of the spike pierces seal 25. The channels or grooves 29 are shown as being straight; however, they may if desired extend in helical fashion about the spike to provide controlled resistance to the discharge of pressurized gas from the cartridge 21. The piercing member 26 is shown in retracted position in FIG. 2. It may be extended to rupture the seal of the capsule by rotating the knob or handle 30 of operator 31. The operator also includes a shaft 32 which is rotatably mounted in transverse bore 33 of body section 11 and which is retained therein by O-ring 34 (FIG. 3). The shaft includes a cam portion 35 disposed within the expansion chamber and engagable with the front face of piston 26a to drive the piston rearwardly into its extended position as the knob 30 is rotated. Helical compression spring 36, interposed between the rear face of piston portion 26a and an internal shoulder 27 formed at the entrance of the expansion chamber, urges member 26 forwardly into its retracted position as soon as cam 35 has been rotated out of engagement with piston portion 26a. In the embodiment illustrated, cam 35 takes the form of a triangular node projecting radially from shaft 32 so that the piercing member will be in its fully extended position for only a small portion of the cam's angular sweep.

A resilient collar 38 extends about the mid-portion of body section 11 to provide a hermetic seal against mouthpiece 39. The collar may be formed of rubber or any other resilient material and may be secured against rearward displacement along body section 11 by means of a shoulder 40.

The fixed orifice 17 of nozzle 16 is dimensioned to permit the release of pressurized contents from the device into the spirometer over an interval of no greater than about five seconds. The preferred interval is approximately three seconds which conforms generally to the time period of a Forced Expiratory Volume (FEV) test where a subject maximally inspires air and then forcefully exhales all of his distendable lung volume as quickly and completely as possible. Where cartridge 21 is charged with a sufficient quantity of liquid carbon dioxide to generate approximately 5 liters of gas at standard temperature and pressure, an orifice diameter within the range of 0.005 to 0.02 inches might be used, the preferred diameter being approximately 0.01 inches.

FIG. 8 is an exponential volume/time curve of the type recorded by a spirometer tested in accordance with this invention. Such a curve is also similar to the volume/time curve generated when the spirometer is used to test a subject Forced Expiratory Volume (FEV) and Forced Vital Capacity (FVC). The applicable equation is as follows:

$$VOL_t = FVC(1 - e^{-t/k})$$

where FVC represents Forced Vital Capacity, t represents time in seconds, k is a time constant in seconds which is inversely related to orifice size, and $VOL_t$ represents volume at a given time in liters.

The flow rate in liters per second may be written as:

$$FLOW = (FVC/k)e^{-t/k}$$

and the peak flow in liters per second (PEFR) may be expressed as:

$$PEFR = FVC/k$$

It is to be understood that when a spirometer is tested with the calibration device disclosed herein, the FVC value is the volume in liters of gas discharged into the spirometer. The following chart sets forth illustrative examples of the different values obtainable by altering orifice size to obtain different time constants. Corresponding curves A, B, C are illustrated in FIG. 8 when using a constant pressure-volume source of 5 liters (FVC):

|   | FVC | k   | FEV 1% | PEFR |
|---|-----|-----|--------|------|
| A | 5.0 | 0.4 | 91.8%  | 12.5 |
| B | 5.0 | 1.0 | 63.2%  | 5.0  |
| C | 5.0 | 2.4 | 34.1%  | 2.08 |

A time constant of 1.0 is achieved with an orifice diameter of approximately 0.010, yielding a peak flow rate (PEFR) of 5.0 liters per second and a discharge into the spirometer of 63.2% of the total volume in the first second of discharge. Such flow and volume characteristics are represented by the curves in FIG. 8 which also reveals that the flow rate drops off sharply (exponentially) as the test continues.

It is believed apparent from the above that this device provides a simple and inexpensive means for calibrating spirometers on a day-to-day basis, providing precisely repeatable time/volume (or flow/volume) curves, and also providing information useful in establishing timing speed and BTPS correction. A user is therefore able to make valid comparisons between the charts reproduced for a given patient at different times by the same spirometer or by different spirometers. Not only does such calibration permit valid comparative analysis of spirometric tests but, as brought out above, gives the doctor or other operator a basis for ascertaining the accuracy and reliability of his spirometric equipment.

The filter element 19 shown in FIG. 2 is of cylindrical configuration and functions only as a filter to prevent ice particles and other particulates from entering and possibly obstructing orifice 17. In some instances, however, as where a spirometer is to be calibrated for assessing abnormal pulmonary function characteristics (where a non-linear exponential wave form would be observed), the filter may take the form of a porous sintered metal cup 119 shown in FIG. 2A. The cup is threadedly secured to nozzle 116 which has a fixed orifice 117. A plunger in the form of ball 150 is normally seated within the cavity of the cup under the influence of compression spring 151. As gas is discharged into chamber or passage 13 from a suitable pressurized cartridge 21, the initial force of the flow unseats the ball, shifting it towards orifice 117 and reducing the surface area of the filter through which the gas must pass as it travels toward the orifice. As the flow rate diminishes, the spring acts to urge the ball back towards its seated position as shown, thereby increasing the effective filter area. The cup-shaped filter and spring-loaded plunger (ball) thus provide a variable entry of gas to the orifice 117 which is inversely related to the exponential pressure generated.

FIG. 7 shows the device 10 in conjunction with a spirometer S, the spirometer being equipped with a breath isolator 42 of the type disclosed in detail in U.S. Pat. No. 3,512,521, the disclosure of which is incorporated by reference herein. The isolator comprises a housing 43 having an inlet in the form of mouthpiece 44 and an outlet 45 leading to the spirometer. The calibration device 10 is coupled to mouthpiece 44 in the same manner indicated in FIG. 2. Within housing 43 is an expandable bag or membrane 46 which is in flow communication with mouthpiece 44 and which effectively divides the interior of the housing into two chambers, one chamber being the interior of bag 46 and the other being the space within the housing external to the bag.

Since the housing is sealed except for inlet 44 and outlet 45, the forceful expansion of the bag 46 because of the discharge of expanding gas from cartridge 21 will result in the displacement of essentially the same volume of air from outlet 45 into spirometer S. However, by interposing isolator 42 between device 10 and spirometer S, the gas discharged into the spirometer will have a composition and viscosity closer to that of air normally expired from a patient. In addition, the flow of air through outlet 45 and into the spirometer is more uniform throughout the full cross sectional area of such flow passages than would be obtained if the isolator 42 were omitted and the device 10 were coupled directly to spirometer S (as in FIG. 2).

While FIG. 7 shows the device 10 communicating with the interior of bag 46 and the spirometer S communicating with that portion of the interior of the housing external to the bag, the two might be reversed so that the spirometer communicates with the bag's interior. Such a reversed arrangement permits the bag to be pre-filled with any selected gas (or gases) having moisture content, composition, and other parameters tailored to suit the operating characteristics of the particular spirometer to be tested.

The housing or cannister 43 may be equipped with a heater 47, such as a conventional thermostatically-controlled crystal heat generator or "crystal oven", for warming the air within the housing to approximately 98.6° F. The use of such a heater eliminates the need for making BTPS correction, since the air displaced from the cannister into the spirometer will be at body temperature and at barometric pressure, and differences in moisture content are not of major significance.

Referring to FIGS. 9 and 10, the calibrating device 50 depicted therein is similar to the device already described except that the body section 51 is utilized as a container to hold the pressurized gas within the device until a calibrating procedure is to be commenced. As before, a pressurized cartridge 21 is supported in a cartridge-receiving section 52 threadedly connected to body section 51. However, the spike 53 secured to the body section is hollow and is positioned to pierce the seal of the cartridge as the two sections 51 and 52 of the holder are threaded together. Therefore, when the parts are disposed as shown in FIG. 10, the seal of the cartridge has been broken and the contents of the cartridge have expanded into chamber 51a.

The nose portion 54 of the holder is shown to be stepped for the purpose of forming a fluid-tight seal with the mouthpiece of a spirometer but, if desired, the nose portion may have the same configuration, and may form a fluid-tight seal with a mouthpiece in the same manner, as the nose portion 15 of the previous embodiment. A nozzle 55 having a fixed orifice 56 is threadedly secured within the flow passage 57 of the nose section and performs the same function as previously-described nozzle 16.

In the modified construction, the gas-releasing means takes the form of a manually-operable valve 58 interposed along the body section between nose portion 54 and the expansion or conversion chamber 51a. The valve member is provided with an apertured stem 58a rotatably received within a transverse bore 59. Handle 58b may be shifted between the longitudinally extending position shown in FIG. 9, in which the aperture of the stem is aligned with flow passage 57a to open the valve, and a transversely-extending position shown in FIG. 10 in which the opening of the stem extends transversely to close the valve and thereby block the escape of gas from chamber 51a.

It will be observed that gas escaping from cartridge 21 into chamber 51a must pass through a filter element 60 which may be indentical in composition to previously-described filter element 19. Such filter functions to prevent ice particles from passing through chamber 51a and from entering and possibly obstructing orifice 56. Also, in the form illustrated, the body section or container 51 is provided with a relief valve 61 and a pressure gauge 62, both of which are located downstream of filter 60 and are therefore protected by that filter.

Valve 61 is a standard relief valve preset to open at any pressure exceeding the designated pressure for the gaseous contents of chamber 51a. For example, the relief valve may be set to open at pressures exceeding 300 psi, or at any selected pressure within the range of approximately 60 to 600 psi. Whatever maximum pressure is selected for chamber 51a, that pressure must be substantially lower than the pressure of the contents of cartridge 21 before rupture of the cartridge's seal, and lower than the pressure that would be generated in chamber 51a (in the absence of relief valve 61) upon rupture of that seal. The particular pressure selected for chamber 51a depends also upon the volume of that chamber, the purpose in any event being to insure a precise volume of gas for discharge into a spirometer through orifice 56.

Effective results have been obtained with a device having an expansion chamber 51a of approximately 125 cc equipped with a relief valve 61 set to open at pressure in excess of 400 psi, and with a nozzle having a fixed orifice 56 of 0.07 inches, resulting in a device which is capable of releasing approximately 5 liters of gas (when valve 58 is opened) at standard temperature and pressure, and at essentially exponentially diminishing flow rates, over a time interval of approximately three seconds. While specific times, volumes, and pressures are given for purposes of illustration, it will be understood that such values may be varied considerably and that whatever practical values are selected for any given device, that device will then deliver precise reproducible volumes of gas at substantially exponentially diminishing flow rates to the spirometers being calibrated.

Gauge 62 is intended mainly to provide visual verification of proper operation of the device and may be omitted if such verification is not required or desired. Since chamber 51a is relatively large with respect to the volume of cartridge 21 (the volumetric ratio may be within the range of 6:1 to 20:1), the expansion of gas within that chamber is accompanied by a substantial cooling effect. By forming the walls of the body section 51 of aluminum or other temperature absorbing metal, and by adopting an operating procedure in which a timed interval (ordinarily within the range of 1 to 4 minutes) takes place between the piercing of the cartridge and the opening of valve 58, the body or container 51 functions as a heat sink to absorb cold from the gaseous contents. Such a timed delay may be desirable to eliminate any possibility of icing and occlusion of the orifice 56 during a calibration procedure.

It is believed apparent that the equations set out in connection with the first embodiment are also applicable to the operation of the form depicted in FIGS. 9 and 10. Also, since both devices are suitable for use with carbon dioxide cartridges, the isolator 42 previously described in connection with the first embodiment may be used to an advantage with the second embodiment.

Figure 12:
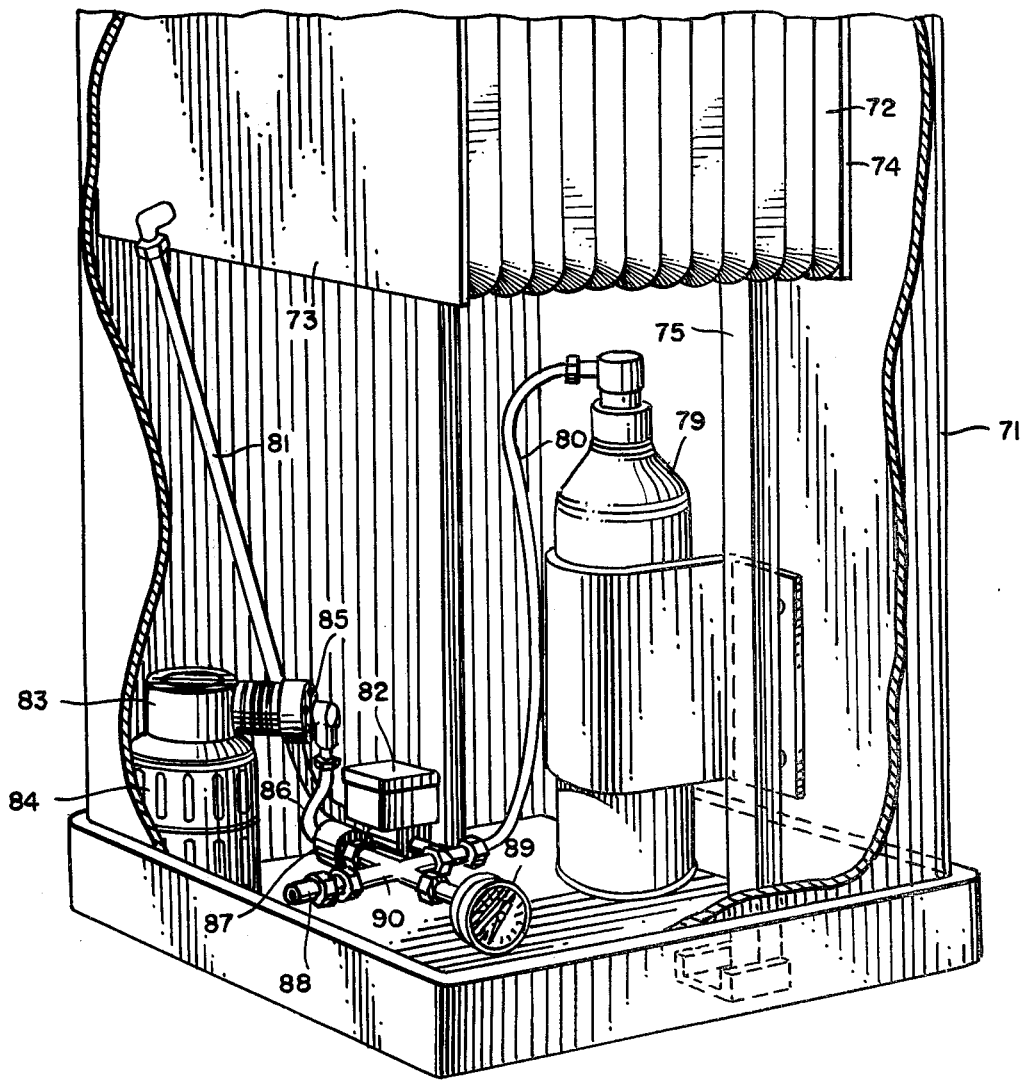
FIG. 12 is a fragmentary perspective view showing the interior of the spirometer casing and, in particular, the instrument-calibrating device.
Figure 13:
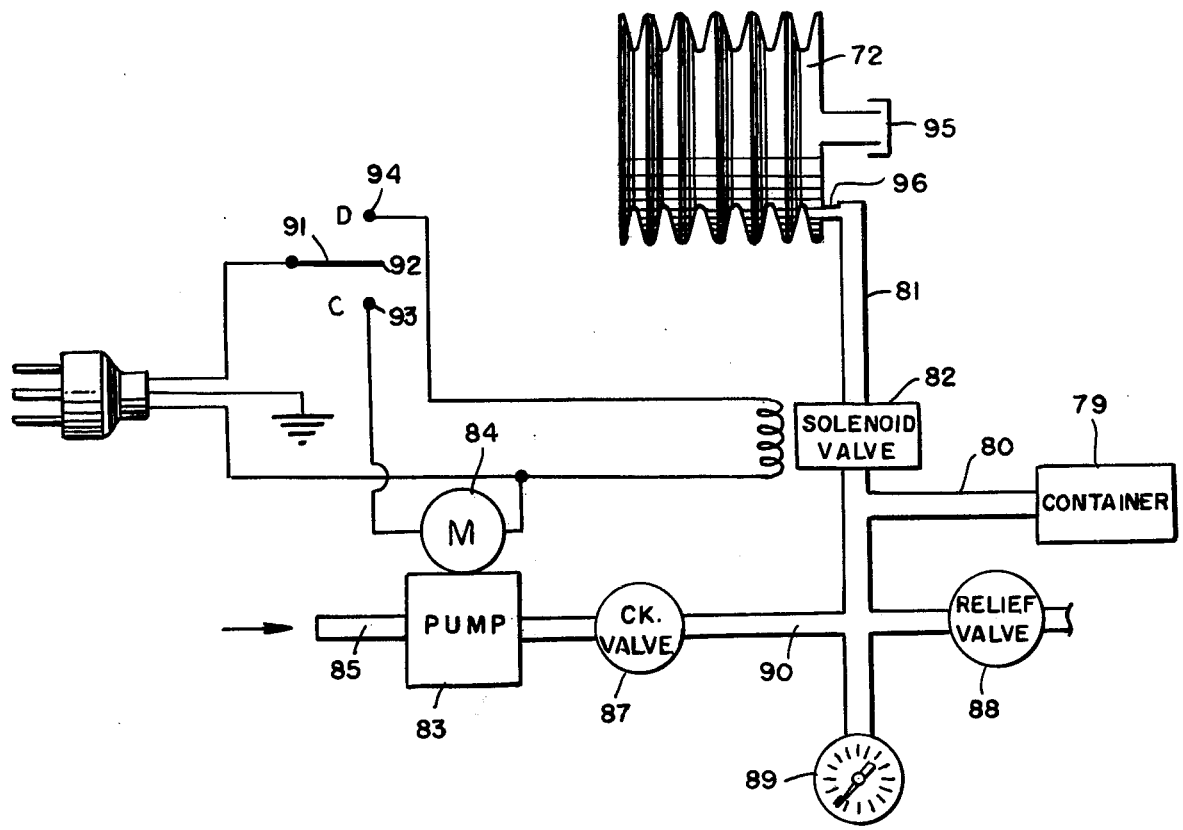
FIG. 13 is a diagram of the fluid flow and electrical circuits of the apparatus depicted in FIGS. 11 and 12.

FIGS. 11–13 are directed to a calibrating device which does not utilize disposable pressurized cartridges but instead includes a reusable container which is pressurized in advance of each instrument-calibrating procedure by means of a suitable pump. Numeral 70 generally designates a spirometer having an upstanding casing 71 which houses a bellows 72. The bellows has a fixed plate 73 and a movable plate 74, the movable plate being supported by a pair of upstanding arms 75 which are pivotally supported at their lower ends as shown most clearly in FIG. 12. A breathing tube 76 communicates with the expandable chamber of the bellows 72 through fixed plate 73, and an arm 77 is joined to the movable plate of the bellows for operating a suitable recording device 78 during pulmonary function tests. As well known in the art, other types of recording devices, such as electronic measuring and recording devices, may be substituted for the one shown.

The spirometer so far described is disclosed in greater detail in U.S. Pat. No. 3,086,515; further description of the spirometer itself is therefore believed unnecessary herein. It is to be pointed out, however, that the bellows-type spirometer is shown simply as one type of spirometer with which the calibrating device or apparatus of this invention may be used and that other types, such as a conventional liquid-supported cannister system, may be substituted.

The instrument-calibrating system of this embodiment is depicted most clearly in FIGS. 12 and 13. That system includes a rigid container 79 for holding a precise volume of gas at a predetermined elevated pressure, conduit sections 80 and 81 for conveying the pressurized gas from the container to the expandable chamber of the bellows 72, a solenoid valve 82 which is normally closed to maintain the selected pressure within the container but which is opened during an instrument-calibrating procedure to allow the pressurized gas to flow from the container to the bellows, and a pump 83 for pressurizing the gas (air) in container 79.

The functional relationship of parts is revealed by FIG. 13 where it will be seen that the positive-displacement pump 83, operated by electric motor 84, draws ambient air into intake 85 and pumps it into conduit section 86. A check valve 87 is interposed along conduit 86 to prevent the backflow of pressurized gas. The maximum pressure of air in line 86 is controlled by relief valve 88, and verification of the accuracy of operation of that valve, as well as the operation of the system as a whole, is revealed by pressure gauge 89. Since conduit section 86 is in communication with conduit section 80 through branched connector 90 (FIG. 12), the maximum pressure controlled by relief valve 88 and displayed by gauge 89 is the pressure existing within container 79 when the system is operating and the solenoid valve 82 is in its normally closed position.

To charge the container 79 with air at the predetermined pressure, operating level 91 (FIGS. 11 and 13) is shifted into its "charge" position to close contacts 92 and 93 and energize electric motor 84. The increase in pressure within container 79 is revealed by gauge 89. When cessation of needle movement reveals that the selected pressure for testing has been attained, the operator switches the operating lever 91 into its discharge position, opening contacts 92 and 93 to interrupt pump operation and closing contacts 92 and 94, thereby energizing the solenoid valve into its opened position. Gas under pressure flows from the container 79, and from the passages of conduit sections 80, 86 and 30 downstream of check valve 87, into conduit 81 and into the expandable chamber of bellows 72.

Before conducting such a test the operator must, of course, seal off the passage of mouthpiece 76 so that the pressurized gas entering the bellows through conduit section 81 will not leak from the bellows. Any suitable closure, such as the cap 95, may be used.

A flow restrictor or orifice of fixed size is located in the flow passage between container 79 and the bellows, such restrictor being represented in FIG. 13 by the reduced portion 96 of the flow passage immediately adjacent bellows 72. The restrictor controls the duration and rate of flow of gas into the bellows, the orifice size, container volume, and maximum pressure being selected to approximate the exponential volume/time curve generated when the spirometer is used to test a subject's Forced Expiratory Volume (FEV) and Forced Vital Capacity (FVC). The applicable equations have already been discussed in connection with the first embodiment.

The fixed orifice 96 should be dimensioned to permit the release of the pressurized contents of the container 79 over an interval no greater than about five seconds. The preferred interval is approximately three seconds which conforms generally to the time period of a Forced Expiratory Volume (FEV) test when a subject maximally inspires air and then forcefully exhales all of his distendible lung volume as quickly and completely as possible. To achieve such results, it is believed apparent that the orifice size must be considered in relation to the fixed volume of container 79 and the maximum pressure generated within that container. In general, containers having volumes within the range of about 0.5 to 2.0 liters, maximum pressures not exceeding about 150 psi, and orifice diameters within the general range of 0.05 to 0.2 inches might be used. Particularly effective results have been obtained with a system in which the container has a volume of 1.0 liter, a maximum pressure within that container of 50 psi is generated, and the orifice diameter is approximately 0.17 inches.

Since the compressor or pump 83 is capable of producing pressures well in excess of the maximum pressure allowed by relief valve 88, the relief valve is the controlling element in assuring reproducibility or uniformity of performance. Any excess air that might otherwise be pumped into the system by compressor 83 is bleed off by the pressure relief valve 88 until the pressure assumes the preselected value. While the source of pressurized air is shown to be a pump or compressor 83 located within the casing of the spirometer, it is to be understood that such source might instead be a high pressure cartridge of the type disclosed in connection with the embodiments of FIGS. 1–10 or, alternatively, a remote compressor used, for example, to pressurize the air or other gas in the pressure lines in hospitals, clinics, and the like.

In describing each embodiment of this invention, reference has been made to the provision of an orifice of fixed or predetermined size. It is to be understood that such an orifice must be of fixed or constant size only throughout a calibration procedure and that someone testing a spirometer might wish to conduct successive tests using orifices of different size, and hence, producing different time constants (see graph of FIG. 8, for example). Hence, a calibrating device or apparatus might be appropriately constructed to permit the quick interchange of nozzles of different orifice sizes or, alternately, to permit adjustment of an orifice into different selected sizes, so that tests producing different time/volume curves might be run. During each test, however, the orifice size would remain "fixed" and the flow would diminish at an exponentially diminishing rate over a selected interval that would normally be less than 5 seconds but might, in certain tests, be as long as 20 seconds.

While in the foregoing I have disclosed embodiments of the invention in considerable detail for purposes of illustration, it will be understood by those skilled in the art that many of these details may be varied without dpearting from the spirit and scope of the invention.

I claim:

1. A device for calibrating pulmonary function testing equipment comprising a container defining a chamber for containing a predetermined volume of gas at a preselected pressure, gas discharge conduit means communicating with said container and including a flow-restricting orifice of predetermined size for the discharge of gas from said chamber, and means normally preventing said discharge of gas but being selectively operable to release said gas through said flow-restricting orifice at reproducible and substantially exponentially diminishing flow rates into a spirometer for calibrating the same.

2. The device of claim 1 in which said container comprises a cartridge having a piercable seal and containing a precisely measured volume of gas under pressure.

3. The device of claim 2 in which said means selectively operable to release said gas comprises a movable piercing element adapted to be shifted into contact with the seal of said cartridge to rupture the same.

4. The device of claim 3 in which said piercing element has external and generally longitudinally-extending channels for the flow of gas therealong.

5. The device of claim 1 in which said container is adapted to communicate with a source of gas under pressure and said chamber comprises an expansion chamber of fixed predetermined volume, said means for releasing gas through said orifice comprising a valve in said gas discharge conduit means between said chamber and said orifice.

6. The device of claim 5 in which said source of gas is included as a component of said device and comprises a cartridge of fixed volume containing gas under pressure, said cartridge having a piercable seal, and hollow piercing means provided by said container and adapted to pierce the seal of said cartridge to place said container and cartridge in flow communication.

7. The device of claim 5 in which said source is included as a component of said device and comprises an air compressor.

8. The device of claim 5 in which a relief valve communicates with said chamber of said container and prevents the buildup of pressure within said container beyond a predetermined pressure.

9. The device of claim 8 in which a pressure gauge communicates with said chamber to display the pressure developed therein.

10. The device of claim 1 in which said container is formed of a metal of high thermal conductivity.

11. A pulmonary function testing equipment calibration device for discharging a predetermined volume of gas at exponentially decreasing flow rates, comprising a holder having separable body and cartridge-receiving sections, said cartridge-receiving section having a cavity for receiving a pressurized gas cartridge and said body section having an expansion passage leading to an orifice of predetermined size for the expansion of gas released from a cartridge and for the discharge of such gas from said holder, piercing means provided by said holder for piercing the seal of a gas cartridge received within said chamber, and operating means for causing said piercing means to pierce the seal of a gas cartridge received within said cavity.

12. The device of claim 11 in which said holder includes a resilient external collar for sealingly engaging the mouthpiece of a spirometer.

13. The device of claim 11 in which said holder includes a particulate filter disposed within said body section adjacent said orifice for extracting particles from the flow of expanding gas.

14. The device of claim 13 in which said filter is formed of sintered metal.

15. The device of claim 13 in which a movable plunger cooperates with said filter to reduce the effective filter area in response to the pressure of the gas impinging on said filter, thereby altering the flow into said orifice to generate a non-exponential wave form corresponding generally with that of an abnormal pulmonary condition.

16. The device of claim 11 in which said piercing means is movably mounted within said holder, and said operating means is engagable with said piercing means for moving said piercing means in relation to said cartridge-receiving section for piercing the seal of a cartridge disposed herein.

17. The device of claim 16 in which said piercing means comprises a piercing spike movable longitudinally between extended and retracted positions for piercing the seal of a pressurized gas cartridge.

18. The device of claim 17 in which said spike has channels for the flow of gas therealong.

19. The device of claim 18 in which said spike includes a tapered tip portion, said tip portion being defined by a plurality of converging planar faces.

20. The device of claim 19 in which spring means are provided for urging said spike into said retracted position.

21. The device of claim 17 in which said operating means includes a transverse shaft rotatably mounted upon said body section, a camming element carried by said shaft within said passage for shifting said piercing spike into extended position when said shaft is rotated, and a knob for rotating said shaft.

22. The device of claim 21 in which a pressurized gas cartridge is disposed within said cartridge-receiving chamber.

23. The device of claim 22 in which said cartridge contains from 9 to 14 milliliters of liquid carbon dioxide.

24. The device of claim 23 in which said orifice has a diameter within the range of 0.005 to 0.02 of an inch.

25. The device of claim 23 in which the diameter of said orifice is approximately 0.01 of an inch.

26. In combination, a pulmonary function calibration device comprising a holder having a body section and a cartridge-holding section, said cartridge-holding section having a cavity for receiving a pressurized gas cartridge, said body section having a chamber for the expansion of gas discharged from said cartridge and having an orifice of predetermined size for releasing said gas from said holder, means normally preventing said discharge of gas but being selectively operable to release said gas through said orifice at reproducible and substantially exponentially diminishing flow rates, and a gas isolation housing operatively connected to said holder, said housing having a first chamber provided with an inlet in direct communication with said orifice, a second chamber having an outlet adapted for connection to a spirometer, and a pressure-responsive element movably disposed within said housing and separating said first and second chambers from each other.

27. The combination of claim 26 in which said holder is provided with a resilient external collar sealingly engaging the inlet of said housing to prevent the escape of gas flowing from said orifice into said first chamber.

28. The combination of claim 26 in which said holder includes a particulate filter disposed within said body section for extracting particles from the flow of expanding gas.

29. The combination of claim 28 in which said filter is disposed adjacent said orifice and a movable plunger cooperates with said filter to reduce the effective area in response to the pressure of gas impinging on said filter, thereby altering the flow into said orifice to generate a non-exponential wave form corresponding generally with that of an abnormal pulmonary condition.

30. The combination of claim 26 in which said housing includes thermostatically-controlled heating means for heating air within said housing.

31. The combination of claim 26 in which said pressure responsive element comprises a flexible bag disposed within said housing and communicating with said inlet.

32. A method for calibrating the operation of a spirometer having an expandable chamber adapted to receive air exhaled by a patient undergoing pulmonary function tests, comprising the step of abruptly releasing into said expandable chamber of the spirometer a predetermined volume of pressurized gas from a fixed volume container having a discharge orifice of selected size, said gas being released at substantially exponentially diminishing flow rates over a preselected interval until the pressures within said expandable chamber of said spirometer and said chamber of said container are equalized, to generate a reproducible volume/time curve similar to the curve generated when the spirometer is used to determine the FEV of a normal subject.

33. The method of claim 32 in which said fixed volume container is a gas cartridge having a piercable seal and containing a precisely measured volume of gas under pressure, and said releasing step includes piercing the seal of said cartridge.

34. The method of claim 32 in which said releasing step includes opening a valve associated with said container to release said volume of pressurized gas from said container into said expandable chamber.

35. A method of calibrating the operation of a spirometer having a mouthpiece for receiving air exhaled by a patient undergoing pulmonary function tests, comprising the steps of operatively connecting said mouthpiece to a holder having a closed chamber of fixed volume containing a predetermined volume of gas under pressure, said holder having a discharge orifice of selected size for the release of said gas into said mouthpiece, and thereafter abruptly opening said chamber to release said gas into said spirometer through said orifice at substantially exponentially diminishing flow rates.

36. A method of testing a spirometer to establish the accuracy of flow rate measurements thereof, said spirometer having a mouthpiece for receiving air exhaled by a patient undergoing pulmonary function tests, comprising the steps of operatively connecting said mouthpiece to a holder having an orifice of selected size and containing a cartridge filled with a precisely-measured volume of gas under pressure, said cartridge having a seal capable of being ruptured for releasing said gas and discharging the same through said orifice and into said mouthpiece, and thereafter rupturing said seal while said holder is connected to said mouthpiece to discharge said gas into said spirometer for calibrating the same.

37. The method of claims 35 or 36 in which said spirometer includes an isolation housing having a first chamber communicating with said mouthpiece and a second chamber from which air is discharged for spirometric evaluation, said first and second chambers being separated by a pressure responsive element movably disposed within said housing, said gas under pressure being discharged from said holder into said first chamber to displace a light amount of air from said second chamber.

* * * * *